US010185929B2

(12) United States Patent
Kharraz Tavakol et al.

(10) Patent No.: US 10,185,929 B2
(45) Date of Patent: Jan. 22, 2019

(54) METHOD AND APPARATUS FOR MANAGING PHYSICIAN PROFILE AND HEALTHCARE APPOINTMENT SERVICES

(75) Inventors: Oliver D. Kharraz Tavakol, New York, NY (US); Cyrus E. Massoumi, New York, NY (US)

(73) Assignee: Zocdoc, New York, NY (US)

( * ) Notice: Subject to any disclaimer, the term of this patent is extended or adjusted under 35 U.S.C. 154(b) by 11 days.

(21) Appl. No.: 12/722,728

(22) Filed: Mar. 12, 2010

(65) Prior Publication Data
US 2010/0228564 A1 Sep. 9, 2010

Related U.S. Application Data

(63) Continuation-in-part of application No. 12/210,765, filed on Sep. 15, 2008, now Pat. No. 8,688,466, and
(Continued)

(51) Int. Cl.
*G06Q 10/10* (2012.01)
*G06F 19/00* (2018.01)
(Continued)

(52) U.S. Cl.
CPC .............. *G06Q 10/10* (2013.01); *G06F 19/00* (2013.01); *G06F 19/328* (2013.01);
(Continued)

(58) Field of Classification Search
CPC ........ G06Q 50/22–50/24; G06Q 40/08; G06Q 10/10; G06Q 30/018; G06F 19/328; G06F 19/00; G16H 40/20
(Continued)

(56) References Cited

U.S. PATENT DOCUMENTS 5,471,382 A * 11/1995 Tallman et al. ............... 600/300
6,345,260 B1    2/2002 Cummings
(Continued)

FOREIGN PATENT DOCUMENTS

WO    WO02/056131 A2    11/2004

OTHER PUBLICATIONS

OpenTable.com (http://www.opentable.com/) provides a website (consumer portal) that allows users to book tables at different restaurants. However, to applicant's knowledge, the offered tables are reserved (given up) by the individual restaurants for OpenTable.com, and thus the reserved tables are handled separately from any other available tables the restaurant may have. To applicant's knowledge, the system also does not accommodate different types of bookings, with corresponding durations, of the table allocation, (e.g. it does not allow to book just for drinks, or desserts, or a full dinner.).
(Continued)

Primary Examiner — Robert A Sorey
(74) Attorney, Agent, or Firm — White and Williams, LLP

(57) ABSTRACT

Method and apparatus for the collection and management of healthcare practitioner profile information prior to inclusion in a hospital directory of affiliated practitioners or insurance provider directory of participating practitioners. Healthcare practitioners (e.g., physicians) enter and communicate changes to their profile data to a central database to increase their compliance and decrease the frequency of providing updated or incomplete information in a hospital or insurance provider directory. The profile data can be credentialed according to rules specific to each hospital or insurance provider, prior to inclusion in the directory. The directory may further provide online booking of available appointment times for affiliated physicians from multiple practice
(Continued)

groups. The online booking process can simultaneously be available on multiple websites of a hospital, insurance provider, physician practice group and/or centralized provider (aggregator).

18 Claims, 15 Drawing Sheets

Related U.S. Application Data a continuation-in-part of application No. 12/210,716, filed on Sep. 15, 2008, now abandoned, and a continuation-in-part of application No. 12/210,690, filed on Sep. 15, 2008, now abandoned, and a continuation-in-part of application No. 12/210,664, filed on Sep. 15, 2008, now abandoned.

(51) Int. Cl.
  *G06Q 30/00* (2012.01)
  *G06Q 50/22* (2018.01)
  *G16H 40/20* (2018.01)
(52) U.S. Cl.
  CPC .......... *G06Q 30/018* (2013.01); *G06Q 50/22* (2013.01); *G16H 40/20* (2018.01)
(58) Field of Classification Search
  USPC ........................................................ 705/2–4
  See application file for complete search history.

(56) References Cited

U.S. PATENT DOCUMENTS

| | | | |
|---|---|---|---|
| 6,477,503 B1 | 11/2002 | Mankes | |
| 6,757,898 B1 | 6/2004 | Ilsen et al. | |
| 7,069,228 B1 | 6/2006 | Rose et al. | |
| 7,174,303 B2 | 2/2007 | Glazer et al. | |
| 7,212,985 B2 | 5/2007 | Sciuk | |
| 2002/0065758 A1* | 5/2002 | Henley ................. | G06F 19/328 705/37 |
| 2002/0116220 A1 | 8/2002 | Glazier | |
| 2003/0195838 A1* | 10/2003 | Henley ................. | G06F 19/328 705/37 |
| 2003/0217111 A1* | 11/2003 | McKay ............... | G06F 17/3089 709/207 |
| 2004/0010423 A1 | 1/2004 | Sameh | |
| 2004/0158486 A1 | 8/2004 | Nudd et al. | |
| 2004/0199412 A1 | 10/2004 | McCauley | |
| 2004/0220829 A1* | 11/2004 | Baharav et al. .................. 705/2 | |
| 2004/0236601 A1 | 11/2004 | Summers et al. | |
| 2005/0165627 A1 | 7/2005 | Fotsch et al. | |
| 2006/0129444 A1 | 6/2006 | Baeza et al. | |
| 2007/0083403 A1* | 4/2007 | Baldwin ................ | G06Q 10/10 705/346 |
| 2007/0106752 A1 | 5/2007 | Moore | |
| 2007/0250783 A1* | 10/2007 | Wu ......................... | G06F 19/00 715/762 |
| 2008/0046913 A1* | 2/2008 | Dear ............................... 725/24 | |
| 2008/0114689 A1* | 5/2008 | Psynik et al. ................... 705/51 | |
| 2008/0155456 A1* | 6/2008 | DiRienzo ....................... 715/780 | |
| 2009/0089085 A1* | 4/2009 | Schoenberg ....................... 705/2 | |
| 2009/0164252 A1* | 6/2009 | Morris .................. | G06Q 10/00 705/3 |
| 2012/0123790 A1* | 5/2012 | Kenyon ............................ 705/2 | |

OTHER PUBLICATIONS

NexSched (http://www.nexsched.com/index.html) provides a data synchronization product for online booking of medical appointments. However, to applicant's knowledge, this product allows booking only from one medical practice group. Also, to applicant's knowledge, the product does not cache the availability data, rather it requests information each time a patient starts a query (similar to the SABER travel service). To applicant's knowledge, the product does check for changes before it writes a booking back to the practice database to provide data synchronization.

Xoova—This company previously had a website (consumer portal) for requesting medical appointments from a multiple practice groups. To applicant's knowledge the Xoova website launched sometime in Nov./Dec. 2007 and subsequently folded. To applicant's knowledge, the Xoova platform did not offer standardized appointment types, nor did it offer real/time appointment bookings, because availability was not saved on the Xoova servers. Rather, when the user requested an appointment, the request was transmitted to the provider (group), manually reviewed and responded to.

CAQH, Universal Provider Datasource, one page (http://www.caqh.org).

International Classifications of Diseases for Oncology (ICD-0), nine pages (http://en.wikipedia.org).

SNOMED CT (Systemized Nomenclature of Medicine—Clinical Terms) (http://en.wiki.org/wiki/SNOMED_CT).

The Record, Sep. 10, 2008, "Helping Choose the Right Doctor for You, Vitals.com CEO Found Inspiration in the OR", 2 pages.

The Deal.com, Oct. 13, 2008 "Vitals.com located $4m", 2 pages.

Jun. 6, 2011 International Search Report and Written Opinion in copending and commonly owned PCT/US2011/027207.

May 20, 2011 Office Action in copending and commonly owned U.S. Appl. No. 12/210,716.

Oct. 1, 2010 Office Action in U.S. Appl. No. 12/210,716.

Decision to Refuse a European Patent Application in the European Patent Office Application No. 11721166.4 dated Jul. 20, 2018.

* cited by examiner

Practice    Doctors    Insurance    Billing    Alerter

Doctors & Staff    <Back to list of All Staff

21 — Profile of:
Michael Ahdoot (Doctor)

22 — ZocDoc Username
mahdoot@gmail.com

23 — Professional Statement
www.TheNewYorkEyeDoctor.com
Dr. Ahdoot is a staunch..........
own eye 24 — NPI Number
1033211925

25 — Job Title
• √√ Associate Adjunct Surgeon     34

26 — Department
• √√ Opthamology

27 — Professional Suffixes (Required)
• √√ MD

28 — Specialties (Required)
• √√ Eye Doctor
• √√ Cornea & External Diseases Specialist
• √√ General Eye Doctor Michael Ahdoot's Photo: — 36

[+] [+]
[+] [+]   — 37

◎ ✕
Add Another Photo — 38
[Browse]

Credentialing — 29
√ Approved — 30
○ Rejected — 31
◎ Awaiting Credentialing — 32
(May take 7-14 days)

Your profile will be reviewed by: — 33
o ZocDoc
o New York Eye and Ear Infirmary Only approved items are visible for patients
Unmarked items are automatically approved

Filter: /42

First Name: /43
Last Name: /44
Approval Status: Pending ▼ /45
Doc Status: Any ▼ /46
Provider Package: Any ▼ /47
filter /48

Specialties /50

| Approval Id | Professional Id | Professional Name | Added Specialty | Approve/Reject |
|---|---|---|---|---|
| 100873 | 3292 | Clarissa | Dentist | Approve Reject |
| 99448 | 3244 | Hygenist | Dentist | Approve Reject |
| 103007 | 2872 | Michael Ammazzalorso | Geriatrician | Approve Reject |
| 102193 | 3351 | Luis Ayata | Dermatologist | Approve Reject |
| 103901 | 1398 | Yafit Azizian | Dermatologist | Approve Reject |
| 100218 | 3264 | Stella Bard | Rheumologist | Approve Reject |
| 103076 | 3357 | Hamid Behzadi | Internist | Approve Reject |
| 103077 | 3357 | Hamid Behzadi | Pulmonologist | Approve Reject |
| 101118 | 3304 | Steven Bielamowicz | Ear-Nose-Throat Doctor | Approve Reject |
| 103829 | 3377 | josh brannon | Primary Care Doctor | Approve Reject |
| 104057 | 3384 | Leonid Bukhman | Primary Care Doctor | Approve Reject |
| 103738 | 3374 | Chery; Burgess | Dermatologist | Approve Reject |
| 99926 | 3259 | David R. Capiola | Orthopedic Surgeon | Approve Reject |
| 101128 | 3305 | Houton Chaboki | Ear-Nose-Throat Doctor | Approve Reject |
| 103682 | 3371 | Lawrence Cheung | Dermatologist | Approve Reject |
| 100630 | 3281 | Sammy Chitayat | Endocrinologist | Approve Reject |
| 103507 | 3368 | Mary Conners-Ashmore | OBYGN | Approve Reject |
| 103637 | 2920 | Ralph Delloratta | Sports Medicine Specialist | Approve Reject |

| NY Eye & Ear Infirmary | THE NEW YORK EYE AND EAR INFIRMARY<br>Nation's Most Historic Specialty Hospital...<br>Leader, Innovator, State-of-the-Art Technology | Careers\|Contact\|Directions & Maps\|Make a Digfference<br>🔍 FIND A DOCTOR |

*62*

Departments | Research | About Us | Make a Difference | PATIENTS & PUBLIC | MEDICAL PROFESSIONALS Michael Adhoot, MD —— *65*

*66* — 4902 Queens Blvd
Woodside, NY 11377

☐ 718-565-2020/Phone
718-565-2052/Fax

Practice Name:
Progressive Ophthalmology

*67*

*68* — Specialties:
- Eye Doctor (Ophthalmologist)
- Cornea & External Diseases Specialist Department: —*69*
Ophthalmology Job Title: —*70*
Associate Adjunct Surgeon —*72*

*63*

Insurances Accepted: —*74*
- AARP —*75*
⋮
- View All Plans —*76*

Professional Statement:
www.TheNewYorkEyeDoctor.com
Dr. Ahdoot is a staunch.......
...........................
Supported...more... —*77*

Education: —*78*
- Faculty of ...............
...........................
(Fellowship)

Languages Spoken: —*79*
- English
- Farsi
- Spanish

Board Certifications: —*80*
- The American Board of Ophthalmology

Professional Memberships: —*81*
- American Academy of Ophthalmology
⋮
- New York State Ophthalmological Society States Where Licensed: —*82*
- New York Web Site: —*83*
- http://TheNewYorkEyeDoctor.com Click on a time below to book an appointment Your Visit Reason: [General Eye Consultation ▼]

📍 4202 Queens Blvd
Woodside, NY 11377
View Directions

☐ 718-565-2020/Phone
718-565-2052/Fax

◀ Sunday | Monday | Tuesday | Wednesday | Thursday | Friday | Saturday ▶
01/17/2010 | 01/18/2010 | 01/19/2010 | 01/20/2010 | 01/21/2010 | 01/22/2010 | 01/23/2010

9:30 am
⋮
more

9:30 am
⋮
more

Script for: Premier Dental Associates of Lower Manhattan

```
<div>
<a href="http://www.zocdoc.com/practice/premier-dental-associates-of-lower-manhattan-1037" id="zocdoc_schedule" target='_top'>Find Practice Premier Dental Associates of Lower Manhattan Doctors on ZocDoc</a>
<script type="text/javascript"
src="http://offsiteSchedule.zocdoc.com/remote/Schedule2.js.aspx?providerid=1037&prefix=zocdoc_&bookBtn=" ></script>
</div>
```

```
ZocDocBETA  Currently logged in as:
            Mark Dettelbach (The Feldman E.N.T. Group, P.C.)
```

Login To Practice: [          ]   Choose a location [6410 Rockledge Drive ▼]

| Working Hours | Configuration | Availability Grid | Logs |

[Settings] [Professional Mappings] [Location Mappings] [Appointment Type Mappings]
○ Practice Management Settings Local Location                    ZocDoc Location —164
        162   1-BB Office(1) >> Barlow Building-5454 Wisconsin Avenue
              2-DC Office(7) >> DC-1145 19th Street NW
              3-Germantown Office(2) >> Germantown-20528 Boland Farm Road
              4-Bethesda Office(12) >> Champlain Building-6410 Rockledge Drive
              5-Ambulatory Surgery Center(3) >> Not Mapped
              6-Children's Hospital(6) >> Not Mapped
              7-Georgetown University Hospital(11) >> Not Mapped
              8-River Road Surgery Center(8) >> Not Mapped
              9-Siblev Hospital(9) >> Not Mapped
              A-Washington Hospital Center(10) >> Not Mapped ( Save )

FIG. 12

| 172 | 174 | | | 176 | 170 |
|---|---|---|---|---|---|
| Radiologist(123)-> Abdominal Radiologist (271) | CT Scan-Other(245) | Active ☑ | Available ☑ | 1 | Member of Radiologist(123),General Radiologist(208), Pediatric(265),Abdominal Radiologist(271), |
| Radiologist(123)-> Abdominal Radiologist (271) | Barium Swallow(1251) | Inactive ☐ | Available ☑ | 255 | Member of Abdominal Radiologist(271) |
| Radiologist(123)-> Abdominal Radiologist (271) | CT-Scan-Virtual Colonoscopy(243) | Active ☑ | Available ☑ | 255 | Member of Radiologist(123),General Radiologist(208), Abdominal Radiologist(271), |
| Radiologist(123)-> Abdominal Radiologist (271) | Mesenterial Angiography(1250) | Inactive ☐ | Available ☑ | 255 | Member of Abdominal Radiologist(271) |
| Radiologist(123)-> Abdominal Radiologist (271) | MRI-Other(249) | Active ☑ | Available ☑ | 255 | Member of Radiologist(123),General Radiologist(208), Pediatric(265),Abdominal Radiologist(271), Musculoskeletal Radiologist(286), |
| Radiologist(123)-> Abdominal Radiologist (271) | Sonography/ Ultrasound(256) | Active ☑ | Available ☑ | 255 | Member of Radiologist(123),General Radiologist(208), Ultrasound/Sonography Specialist(264), Pediatric Radiologist(265), Abdominal Radiologist(271), |
| Radiologist(123)-> Abdominal Radiologist (271) | X-Ray(251) | Active ☑ | Available ☑ | 255 | Member of Radiologist(123),General Radiologist(208), Pediatric Radiologist(265),Abdominal Radiologist(271), Musculoskeletal Radiologist(286) |
| Psychiatrist(122)-> Addiction Specialist (298) | Addiction(177) | Active ☑ | Available ☑ | 1 | Member of Psychiatrist(122),Child and Adolescent Psychiatrist(250),Child and Adolescent Psychiatrist(251), Adolescent Medicine Specialist(253),Addiction Specialist(298) |

Continued From Fig. 13A

| | | | | |
|---|---|---|---|---|
| Psychiatrist(122)-><br>Addiction Specialist<br>(298) | Alcoholism(1246) | Inactive ☐ | Available ☑ | 255 | Memeber of Addiction Specialist(298) |
| Pediatrician(100)-><br>Adolescent Medicine<br>Specialist(253) | Adolescent Medicine<br>Consultation(1133) | Inactive ☐ | Available ☑ | 1 | Member of Adolescent Medicine Specialist(253), |
| Pediatrician(100)-><br>Adolescent Medicine<br>Specialist(253) | Acne(86) | Active ☑ | Available ☑ | 255 | Member of Dermatologist(101),Adolescent Medicine<br>Specialist(253), |
| Pediatrician(100)-><br>Adolescent Medicine<br>Specialist(253) | Addiction(177) | Active ☑ | Available ☑ | 255 | Member of Psychiatrist(122),Child and Adolescent<br>Psychiatrist(250),Child and Adolescent Psychiatrist(251),<br>Adolescent Medicine Specialist(253),Addiction Spceialist(298), |
| Pediatrician(100)-><br>Adolescent Medicine | Anxiety(494) | Active ☐ | Available ☐ | 255 | Member of Psychiatrist(122),Adolescent Medicine Speicalist(2 |

FIG. 13B

METHOD AND APPARATUS FOR MANAGING PHYSICIAN PROFILE AND HEALTHCARE APPOINTMENT SERVICES

FIELD OF THE INVENTION

The present invention relates to directories that display profiles of healthcare practitioners (e.g. physicians), such as a hospital directory containing profiles of their affiliated physicians, or an insurance provider's directory containing profiles of their participating physicians.

BACKGROUND

Hospital directories with physician profiles are typically provided on a hospital website to enable actual or prospective patients to search for a particular healthcare practitioner affiliated with the hospital by name and/or specialty. The hospital directory generally provides certain background information on the practitioner enabling new patients to consider the specific education, areas of expertise, awards and publications, age, languages spoken, and even a personal statement explaining the physician's particular approach to the practice of medicine. After reviewing such physician profile information in the hospital directory and making a selection, the prospective patient is generally invited to contact the physician's office by telephone or visit the physician's practice group website.

The problem with hospital directories is that they generally do not provide much of the information that the patient would like to know before selecting a physician, such as accepted insurance plan(s), and booking availability. Physicians are often affiliated with multiple hospitals and as a result, providing all of this variable information in any one hospital directory becomes a difficult if not impossible undertaking for both the physician and the multiple hospitals. Each hospital has its own procedures and rules regarding, for example, displaying insurance acceptance, physician credentials, office hours and patient communications, and these procedures/rules may or may not be compatible with those of the other hospitals with which the physicians are affiliated and/or which may or may not conform with the various practice management procedures and rules followed by the physicians in their own offices. The net effect is that hospital directories provide only limited information, and the process of collecting, reviewing and approving that limited information requires significant human resources. As a result, hospital directories are typically in a state of disrepair and provide a very low rate of return on attracting new patients, hospital resource utilization, and ultimately revenue and profit.

Insurance company directories may also contain profiles of their participating physicians and suffer similar problems. Still further, the failure to provide accurate and complete physician profile information can impose even greater costs on the insurance companies. For restricted plans (e.g. an HMO) that require patients (subscribers) to use a doctor within an approved provider list, the insurer is often mandated by state law to provide the subscriber with an appointment within a specified amount of time. Facilitating this process is therefore of paramount importance to the insurer. Still further, a very high percentage of a health insurer's costs are emergency room visits; reducing such visits by its plan members, by enabling a regular office visit instead, represents a huge potential cost savings.

The issues described above have been long-standing problems for both hospitals and insurance companies, and for their patients and physicians.

SUMMARY OF THE INVENTION

According to various embodiments of the invention, apparatus and methods are provided for significantly enhancing the performance, accuracy, utilization and rate of return from hospital directories with profiles of their affiliated physicians, and/or insurance provider directories with profiles of their participating providers.

In one embodiment, apparatus and methods are provided which enable healthcare practitioners (e.g., physicians) to communicate changes to their profile data so as to increase their compliance and decrease the frequency of providing outdated or incomplete information in a hospital or insurance provider directory.

In another embodiment, a credentialing process is provided enabling hospitals and insurance providers to credential the profile information that is provided by the practitioner prior to including such information in their respective directories. The process enables each hospital and insurer to define their own rules for verifying some or all of the profile information provided.

In another embodiment, a reliable method is provided for matching practitioner to entries in insurance directories, such that a practitioner's profile can be more easily updated with complete and up-to-date insurance information.

In another embodiment, an apparatus and method is provided for online booking of healthcare practitioner appointments on multiple websites. This online booking process can occur simultaneously on multiple websites of a hospital, insurance provider, physician practice group, and/or centralized provider (aggregator). When provided with the enhanced directory services previously described, the hospital and insurance provider directories not only provide more complete and up-to-date physician profile information enabling patients to more easily search for and select a desired practitioner, but further allow for the immediate online booking of an appointment with the selected practitioner.

According to one embodiment of the invention, an apparatus is provided which includes:
  a computer apparatus for managing and storing a central managed database of physician profiles for physicians having affiliations with multiple hospitals and/or participations with multiple insurance providers, the database containing multiple categories of physician profile data (PPD) for each physician;
  a portal accessible by computer to physicians over a public network for submitting the PPD to the database; and
  a computer implemented selection filter for retrieving from the database different select categories of the PPD for a specified physician based on the physician's hospital affiliations and/or insurance participations.

In one embodiment, the apparatus further includes:
  a set of computer implemented credentialing rules specific to a hospital or insurance provider for application to the PPD prior to inclusion of the PPD in an on-line physician profile directory of the respective hospital or insurance provider.

In one embodiment, the set includes rules for:
  excluding the selected PPD from the directory;
  including the selected PPD in the directory;

requiring approval by the respective hospital or insurance provider before including the selected PPD in the directory.

In one embodiment, the categories include one or more of:
physician name;
phone number;
practice location;
office hours;
title;
department;
professional suffixes;
board membership;
gender;
specialties;
procedures performed;
insurances;
awards; and
publications.

In one embodiment, the database includes a different unique identifier for each physician.

In one embodiment, the categories include practice location and a geographic indicator of the practice location.

In one embodiment, the apparatus further includes:
a central managed database of available appointments with the physicians.

In one embodiment, the apparatus further includes:
a portal accessible by computer to patients over a public network for booking one of the available appointments.

In one embodiment, the hospital or insurance provider directory includes a link to an aggregator's website providing online booking of appointments with physicians across multiple practice groups.

According to another embodiment of the invention, a method of managing physician profiles is provided which includes:
  providing a portal to enable physicians affiliated with multiple hospitals and/or participating with multiple insurance providers to submit specified categories of physician profile data (PPD) to a central managed database;
  storing and managing the PPD in the central database; and
  providing PPD from the central database for inclusion in an online physician profile directory of a hospital or insurance provider.

In one embodiment, the method further includes:
applying a set of credentialing rules specific to the hospital or insurance provider for determining compliance with the rules of some or all of the PPD and, if compliance is found, including the PPD in an online directory of the respective hospital or insurance provider.

In one embodiment, the method further includes:
providing a different unique identifier for each physician in the database.

In one embodiment, the method further includes:
comparing the provided PPD to the hospital's or insurance provider's existing physician profile data and applying a merge process to create a merged profile.

In one embodiment, the method further includes:
an aggregator managing the central database and allowing shared access to the PPD as a web-based service.

In one embodiment, the method further includes:
an aggregator managing a central database of available appointments with the physicians and providing on-line booking of available appointments with the physicians.

In one embodiment, the method further includes:
simultaneously providing the available appointments for online booking on a plurality of websites hosted by two or more of the aggregator, hospital, insurance provider, and/or physician practice group.

In one embodiment, the method further includes:
providing a link in the hospital or insurance provider directory to the on-line booking process.

In one embodiment, the method further includes:
providing specified procedures available across multiple specialties to enable booking of physician appointments based on a specified procedure and not limited to a specialty.

In one embodiment, the method further includes:
wherein the categories include a practice location, and each location is classified by geographic coordinates.

In another embodiment, a computer-readable storage medium is provided with instructions to one or a plurality of computers for execution of the methods previously described.

In another embodiment of the invention, a method is provided which includes:
  a host providing a hospital online directory of physician profile data (PPD) for physicians affiliated with the hospital;
  the hospital providing a website having a link to a website of the host for accessing the directory;
  wherein the host manages physician profile data for the affiliated physicians of the hospital and provides the profile data in the directory of the hospital; and
  wherein the host manages and provides multiple such directories, each for a different hospital.

In one embodiment the host manages credentialing of the physician profile information prior to inclusion of the PPD in the directory.

In one embodiment the host manages a central database of available appointments for physicians affiliated with multiple hospitals.

In one embodiment each directory on the host website provides online booking of appointments with the hospital's respective affiliated physicians.

According to another embodiment of the invention, a method is provided which includes:
  providing a hospital website having an online directory of physician profile data (PPD) for physicians affiliated with the hospital;
  accessing the online directory and reviewing the physician profile data to identify a physician;
  the hospital website further providing online booking of appointments with the affiliated physicians from multiple practice groups; and
  accessing the online booking process including selecting an available appointment and booking the appointment online.

In one embodiment of the method, the physicians:
have affiliations with multiple hospitals;
practice in multiple practice groups; and/or
participate with multiple insurance providers;
and the PPD undergoes a credentialing process specific to each affiliated hospital, practice group or insurance provider prior to inclusion in a directory of the respective hospital, group or provider.

In one embodiment of the method, the physicians:
have affiliations with multiple hospitals;
practice in multiple practice groups; and/or
participate with multiple insurance providers;

and the online booking process is available on multiple website of the hospital(s); group(s) and provider(s).

BRIEF DESCRIPTION OF THE FIGURES

FIG. 3 is a exemplary webpage from an aggregator's website enabling a physician to enter his/her profile information according to one embodiment of the invention;

FIG. 4 is one example of an entry on a display screen enabling a hospital reviewer to perform a credentialing process according to one embodiment of the invention;

FIG. 5 is one example of a listing in a hospital directory for an affiliated physician according to one embodiment of the invention;

FIG. 8 is one example of a script (software code) for providing an online booking functionality according to one embodiment of the invention;

FIG. 9 is an exemplary webpage from a physician's website for online booking according to one embodiment of the invention;

FIG. 12 is an exemplary webpage for mapping physician location information according to one embodiment; and FIGS. 13A and B are is an exemplary screenshot of select data from an aggregator's database enabling identification of physicians that provide a desired service, irrespective of their specialty or sub-specialty, according to one embodiment.

DETAILED DESCRIPTION

Figure 1:
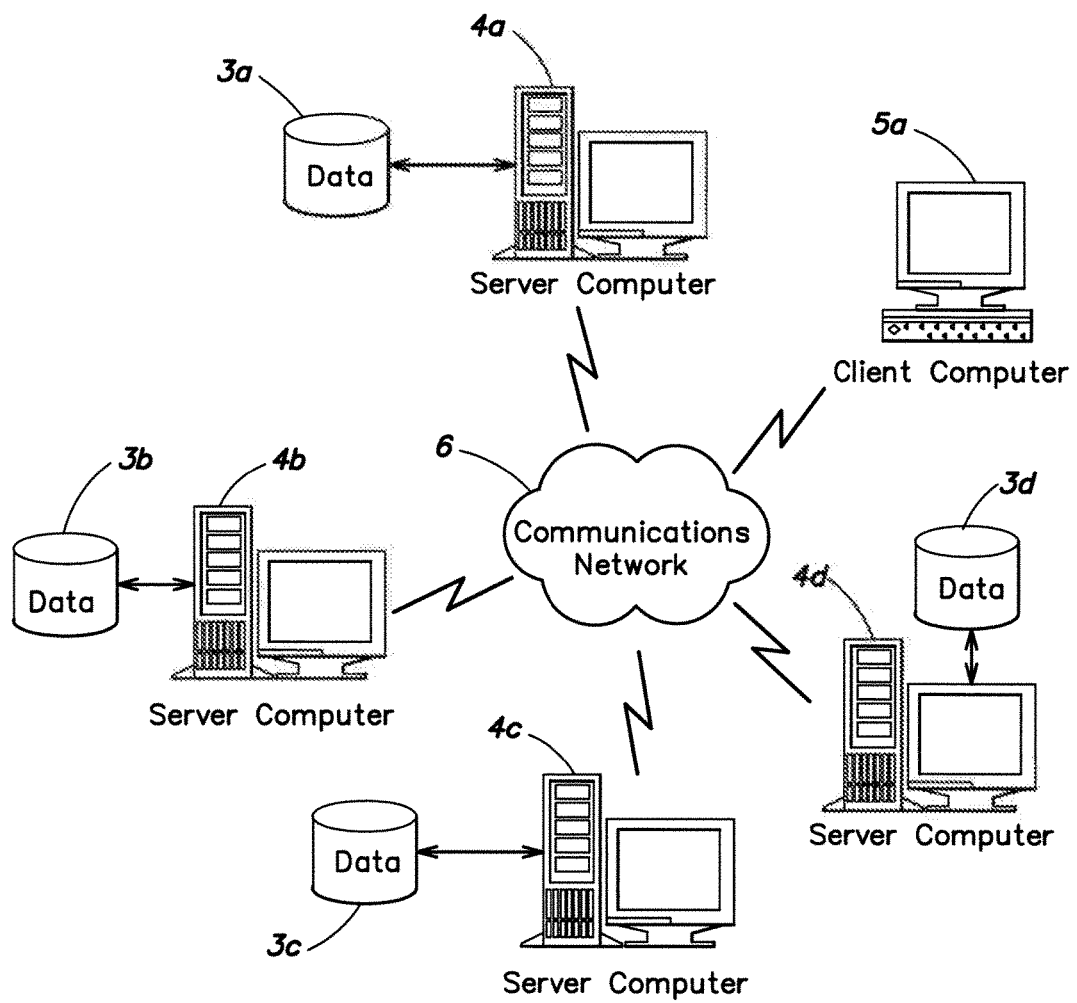
FIG. 1a is a schematic representation of an exemplary communications network for implementing various embodiments of the present invention.

Apparatus and methods are described herein for improving the content of hospital and insurance directories of healthcare practitioners, and for online booking of healthcare appointments on multiple websites, e.g. via a hospital directory website, a physician's practice group website, an insurer's website and/or a centralized service provider's (aggregator's) website. For these purposes, network based communications are required between one or more of the hospitals, insurers, physician practice groups, patients and aggregator. The block diagrams of one such communication system is illustrated in FIG. 1 and is meant to be representative only. Suitable hardware, communication protocols and software languages for implementing the systems and methods of various embodiments of the invention are readily known to those who are skilled in the art and any discussion herein is not meant to limit the scope of the invention.

FIG. 1 illustrates schematically network communications among various server computers 4a, 4b, 4c, and 4d and client computers 5a shown coupled together via a cloud 6 (e.g., the Internet) to communicate with one another using standard communication protocols, such as TCP/IP. The servers can be any type of server, including but not limited to a Windows, Unix, Linux and/or Apple servers. Each server may have an attached data storage system 3a, 3b, 3c and 3d for storing software applications and data.

In accordance with one embodiment of the invention, the network of FIG. 1 allows communications between a centralized service provider (aggregator), multiple hospitals, multiple insurers, multiple healthcare practitioner practice groups, and multiple patients. The aggregator's server provides a network based service to the hospitals, insurers, practitioner groups, and patients, e.g. an aggregator's server 4a provides a web-based data processing service and interface to each of the patient computers 5a, practice group servers 4b, hospital servers 4c, and insurance provider servers 4d, and can also communicate electronically via email with each of these computers and servers. The aggregator's server also communicates (e.g. web-based) with each of the practice groups, hospitals and insurers via their respective servers for retrieving data such as available appointment times and other information for each of the practice groups, hospitals and insurers in order to enable online booking and confirmation of appointments on multiple websites. In alternative embodiments, the aggregator's service is provided to one or more hospitals, one or more insurance providers in addition to the hospital(s), or just to insurance provider(s). For ease of description, the first embodiment will discuss hospitals and not insurance providers, it being understood that the services can similarly be provided to insurance companies.

Figure 2:
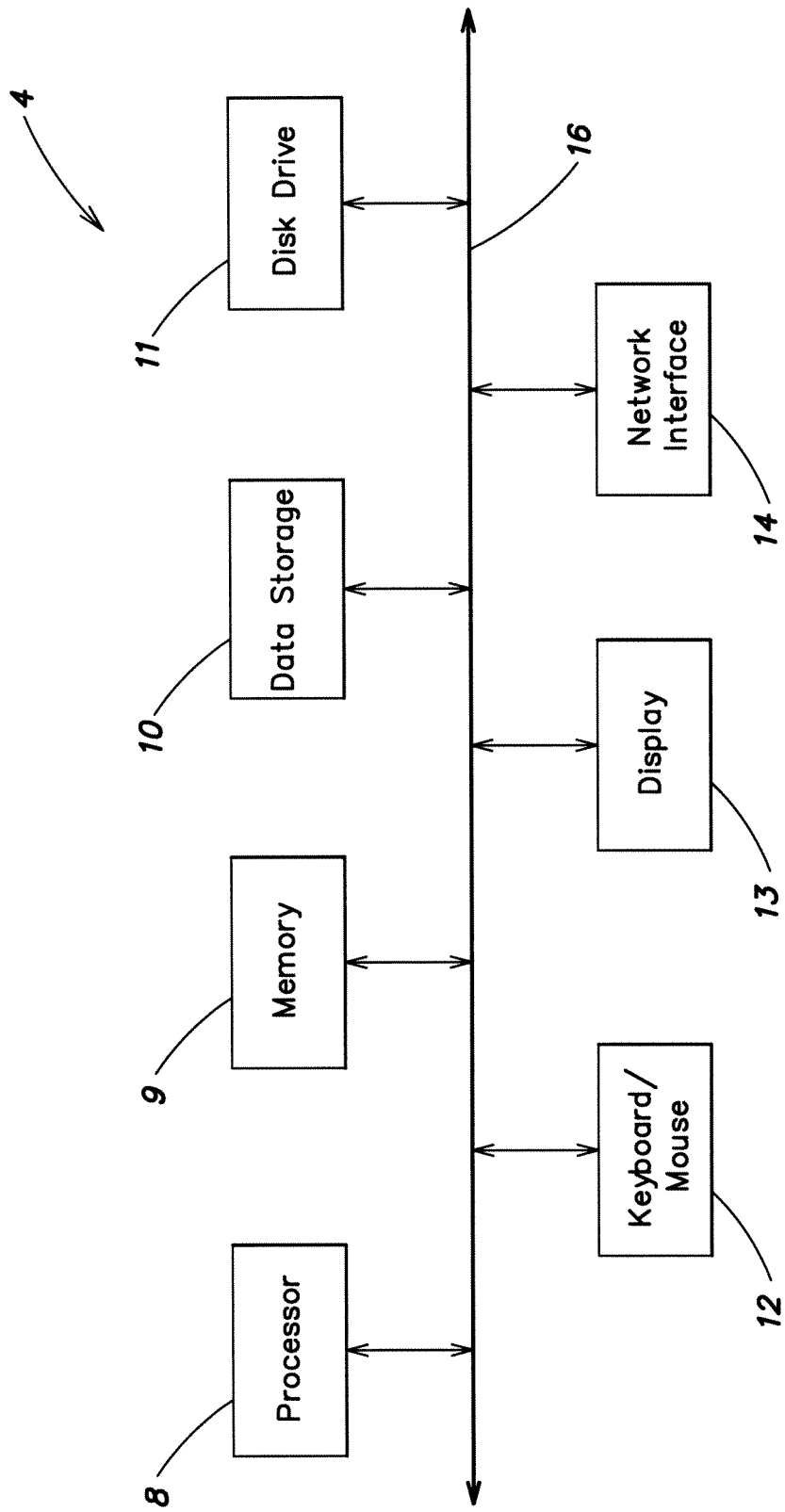
FIG. 2 is a block diagram of an exemplary computer on which the software product(s) of the present invention may be executed.

FIG. 2 is a block diagram of one server 4 which includes a processor 8, memory 9, data storage 10, disk drive 11, keyboard/mouse 12, computer display 13 and network interface 14. The components are coupled together and communicate via a system bus 16. Various software modules of the present invention can be loaded into data storage and during operation are transferred into memory (e.g. RAM) for execution by the processor. A user may manipulate the software and enter commands to the server using the keyboard/mouse. The input/output may be viewed on the display screen. The network interface couples the server to the Internet or whatever type of network is used to connect the server with the other computers and servers of the respective hospitals, practice groups, patients, insurers and aggregator. Further, the server may communicate with a storage array or storage network (e.g. SANS) if there is a need to access large amounts of data. A database of patient records, practice group (practitioner) records, and associated scheduling records may be implemented as a relational database and search engine with, for example, Microsoft's Active Server Page Technology, SQL Server Technology, Database Artisan Software, or database products from Oracle Corp., Redwood Shores, Calif.

The software described herein may be implemented as various modules, e.g. a web module, a database module, an email module, and standard application programming interfaces (APIs). The web module may include a set of templates and icons to enable the creation of web pages. It may include other tools to allow one to create browser friendly websites. These tools enable the creation of dynamic hyper-text web pages to be accessed by the hospitals, patients, practice groups, insurers and aggregator.

The database module may include a relational database and search engine. The records, fields, search queries and other features of the database are described below and suitable alternatives will be apparent to persons who are skilled in the art.

The email module allows emails to be sent to/from patients, practice groups, hospitals, insurers and the aggregator via the respective server/computer. The emails can be sent manually by a person operating the server and can be automatically generated by the server. For example, the email module can be configured to automatically query the database module and send email messages to entities identified in the database module.

The software may include standard APIs so data and other information can be exchanged with other software systems.

Each practice group server may include the group's own practice management software and any other database of information used by the practitioners in that group. As described below, the aggregator may install software on the practice group's server for uploading available appointment times to the aggregator's database and otherwise automating and synchronizing the appointment calendars of the practice group and the aggregator. The relevant appointment booking information may be stored on one or both of the aggregator and practice group servers and data storage systems. Similarly, the aggregator may install software on a hospital's server and/or insurer's server for the same or similar purposes (e.g., exchange of profile information and/or appointment scheduling information).

The database maintained by the aggregator includes records of practitioner profile information and booking information for the practice groups and their respective practitioners, the hospitals and their affiliated practitioners, the insurance providers and their participating practitioners, and each patient who establishes an account with the aggregator. These records will be described further below in various embodiments.

Various systems and methods for aggregating available appointment times for multiple practitioner groups, including search and display algorithms are described in the following co-pending and commonly owned US Patent Applications:

U.S. Ser. No. 12/210,664 filed 15 Sep. 2008 entitled: CENTRALIZED MARKETPLACE FOR HEALTHCARE APPOINTMENTS ACROSS PRACTICE GROUPS;
  U.S. Ser. No. 12/210,690 filed 15 Sep. 2008 entitled: CONSUMER PORTAL FOR HEALTHCARE APPOINTMENTS ACROSS PRACTICE GROUPS;
  U.S. Ser. No. 12/210,765 filed 15 Sep. 2008 entitled: DATA SYNCHRONIZATOIN FOR BOOKING OF HEALTHCARE APPOINTMENTS ACROSS PRACTICE GROUPS; and
  U.S. Ser. No. 12/210,716 filed 15 Sep. 2008 entitled: PATIENT VERIFICATION FOR BOOKING OF HEALTHCARE APPOINTMENTS ACROSS PRACTICE GROUPS.

the entire contents of which are hereby incorporated by reference as if fully set forth herein.

Physician Profile Information

As used in this application, healthcare practitioners includes one or more of physicians, physician assistants, nurses, chiropractors, mid-wives and other providers of healthcare services. As used herein, physicians is meant to include both physicians and other healthcare providers. Patients includes existing patients (of a given healthcare practitioner) and prospective patients.

Physicians and other healthcare providers are frequently affiliated with one or more hospitals. Traditionally, in order to update their profile data, they have been required to separately communicate changes to each hospital with which they are affiliated. In addition, the required profile data may differ for each hospital. This leads to a decrease in practitioner compliance with communicating changes to their affiliated hospitals, and as a consequence means that the hospital directories frequently contain outdated or incomplete information.

According to one embodiment of the invention, an apparatus and method are provided to enable a practitioner to enter their profile information once, to a single database, for all of their affiliated hospitals and practice groups. In this embodiment, an aggregator manages and maintains the database, along with related processes for data entry and retrieval, search, and display. The data fields are standardized so that the data can be used across multiple institutions (hospitals and practice groups) while being input with a single data entry. A data entry mask may be provided that dynamically changes based upon the combination of affiliated hospitals for a given practitioner.

The practitioner profile information is stored in a central database maintained by the aggregator. For ease of description, this embodiment will refer to a physician as the healthcare practitioner, and multiple affiliated hospitals of the physician as the intended recipients of the physician profile information for their respective hospital directories.

Every physician is assigned an individual unique identifier by the aggregator for identification and mapping of data. This identifier can be used for the purposes of enabling the physician to edit his/her own profile information, identify which hospital(s) should receive his/her profile information, and review the status of the credentialing process being performed by the various affiliated hospitals. This identifier is different for each physician in the aggregator's database and facilitates the credentialing process. There is currently no unique identifier for every physician which hospitals, insurance companies and others can use to identify a specific physician. For example, the government assigns an NPI number (National Provider ID) to physicians that accept Medicare and Medicaid patients, but there is no NPI number for doctors who do not accept these government insurance plans. Furthermore, because the NPI system was fairly recently established, there are many physicians who have never updated their profiles to include their NPI number. This has greatly hampered efforts to accurately identify a specific physician across multiple databases.

FIG. 3 is an example of a web page 20 from an aggregator's website which serves as a template for enabling a physician to enter his/her profile information. The physician profile may then be stored as one data record in a central database managed by the aggregator. Here, the web page includes a box 21 identifying the physician by name, a box 22 for his/her username for accessing the aggregator's website, and an entry box 23 for the designated physician to enter a professional statement. Below this, are a plurality of boxes identifying the physician's NPI number 24 and previously entered profile information such as job title 25, department 26, professional suffixes 27, and specialties 28. Beside each entry in the respective profile blocks 25-28, is one of three different credentialing "status" indicators (identified in the right-hand box 29), namely: a check mark for an approved status 30, a minus in a circle mark for a rejected status 31, and a dot in a circle mark for an awaiting credentialing status 32. The physician can thus monitor the status of the credentialing process by the aggregator and the one or more affiliated hospitals (identified in box 33), on the aggregator's website. The profile information further includes a photo 36 of the physician, which is made available to the affiliated hospitals for their directories, and buttons 37, 38 for editing or adding additional photos. An edit button 34 is provided in the various profile information boxes for editing the contents.

The fields presented to a given physician on the aggregator's website changes dynamically depending upon which hospitals the physician is affiliated with. When a doctor enters an additional, previously unknown hospital affiliation on the aggregator's webpage, the additional fields required for this hospital are searched for and obtained in the aggregator's database, and then automatically added to the data entry mask for that physician. Thus, every physician is not required to enter and maintain the entire set of profile information fields available on the aggregator's website and database, but rather the aggregator automatically provides a more limited subset of required profile information for the hospitals affiliated with a given physician. This reduces the time required for the physician to enter the necessary profile information, and thus increases compliance with and the maintenance of up-to-date and complete information.

Each hospital needs to maintain control over which information appears on their directory to ensure both accuracy and relevance for their patients. Typically, a hospital will select only a subset of the available physician profile information to be displayed on its directory, and they may choose to verify some or all of the information provided. This makes it difficult for a doctor with multiple hospital affiliations to determine which data needs to be provided to which hospital. As a result, a hospital has historically employed a team of people to request information from the doctor, manually decide which part of the information needs to be verified, and manually update the hospital directory. This process is costly, slow, error prone and frequently incomplete.

In accordance with one embodiment of the invention, an aggregator provides a service for doctors to enter profile information once to the aggregator's database; the profile information is then made available to various affiliated hospitals of the practitioner but will not be included in a hospital directory until it complies with a set of rules defined by the respective hospital. In one example, these rules can:
  generally exclude select categories of information from the hospital directory;
  automatically post updated information in select categories to the hospital directory;
  require human approval before information in select categories appears in the hospital directory.

These rules can be implemented on a "field" level, i.e., based on individual fields in each data record, and the fields can be standardized for use across different practice groups and hospitals.

The aggregator's database stores a respective item of profile information in an associated field, whether this field is excluded, automatically included, or requires human review by one or more of the affiliated hospitals. In addition, for every item of information provided by a doctor, the aggregator's system stores the status of this item in the database, e.g., automatically excluded, automatically reviewed, pending human review, accepted by a human reviewer, rejected by a human reviewer, and the identity of the human reviewer.

The human reviewer at the respective hospital has credentialing software, provided by the aggregator, to perform the credentialing process. FIG. 4 shows one example of a data entry display screen 40 enabling a hospital reviewer to perform the credentialing process. At the top of the display, a set of five filter windows 42 are provided prompting the reviewer to enter or select from a pull down menu the following items: first name 43, last name 44, approval status 45, document status 46 and provider package 47. The reviewer enters the appropriate information and then clicks the filter button 48, initiating a search of the hospital database for the entered information. Below the filters is a specialties window 50 with five columns across the window, namely, Approval Id 51, Professional Id 52, Professional Name 53, Added Specialty 54, and Approve/Reject 55. Each of these column headings identifies a field for credentialing each practitioner and specialty in the hospital directory. Each row 56 in the window represents a practitioner/specialty pair, enabling the reviewer to approve or reject such pair, prior to inclusion in the hospital directory. The above details are just one example of a credentialing process and not meant to be limiting.

Each hospital maintains its own directory review process whereby profile information provided by the aggregator to the hospital is subject to the hospital's own review and approval prior to acceptance and entry into the hospital directory. Each hospital may maintain different content in their hospital directory, i.e., different fields of profile information for a respective practitioner. FIG. 5 shows one example of a listing from an online hospital directory for an affiliated physician. Below a running head 61 identifying the hospital, and below a series of links identifying various webpages on the hospital website, there is a display 63 of text, photos and graphics concerning one individual physician and his affiliated profile information. This hospital directory also includes a window 64 to enable immediate online booking of an appointment with the associated physician. This online booking feature will be described in a subsequent section.

Here the physician's profile includes, on the upper left-hand side of the webpage, the physician's name 65, contact information 66, link to his practice group website 67, specialties 68, department 69 and job title 70. Next to these windows on the right-hand side, is another window 72 with a geographical display (street map) identifying the location of the practitioner's office by a numbered marker (here identified by the number "1"). In the event that the practitioner has multiple office locations, there would be multiple differently numbered location indicators.

The hospital directory page further includes, along the left-hand margin going from the middle to the bottom of the page, a plurality of text boxes with descriptive profile information and/or links to other web pages on the same or a different website. For example, one box 74 includes a list of the insurances accepted by the physician, with links 75 to the respectively identified insurance plans. Another box 76 contains the physician's professional statement, and a link 77 to a more complete statement. Another box 78 lists the physician's education (schools/degrees). Another box 79 lists the languages spoken by the physician. Another box 80 lists the board certifications. A further box 81 lists the professional memberships of the physician. Another box 82 lists the states in which the physician is licensed. The lowermost box 83 on the left-hand side contains a link to the physician's practice group website.

The profile data entry and credentialing process previously described may be implemented in various apparatus and methods according to various embodiments of the invention. In one such embodiment, the aggregator may send the physician an email containing a link with a unique identifier which when clicked, brings the doctor to a specially prepared webpage that allows the doctor to edit his/her profile. Each identifier is matched to exactly one physician profile. The doctor registers with a password that allows him/her to log in later without requiring an initial email from the aggregator. The unique identifier may be used by each of the aggregator, physician, physician practice group, and physician affiliated hospitals, for obtaining access to profile information in the aggregator's database for a specific physician.

Figure 6A:
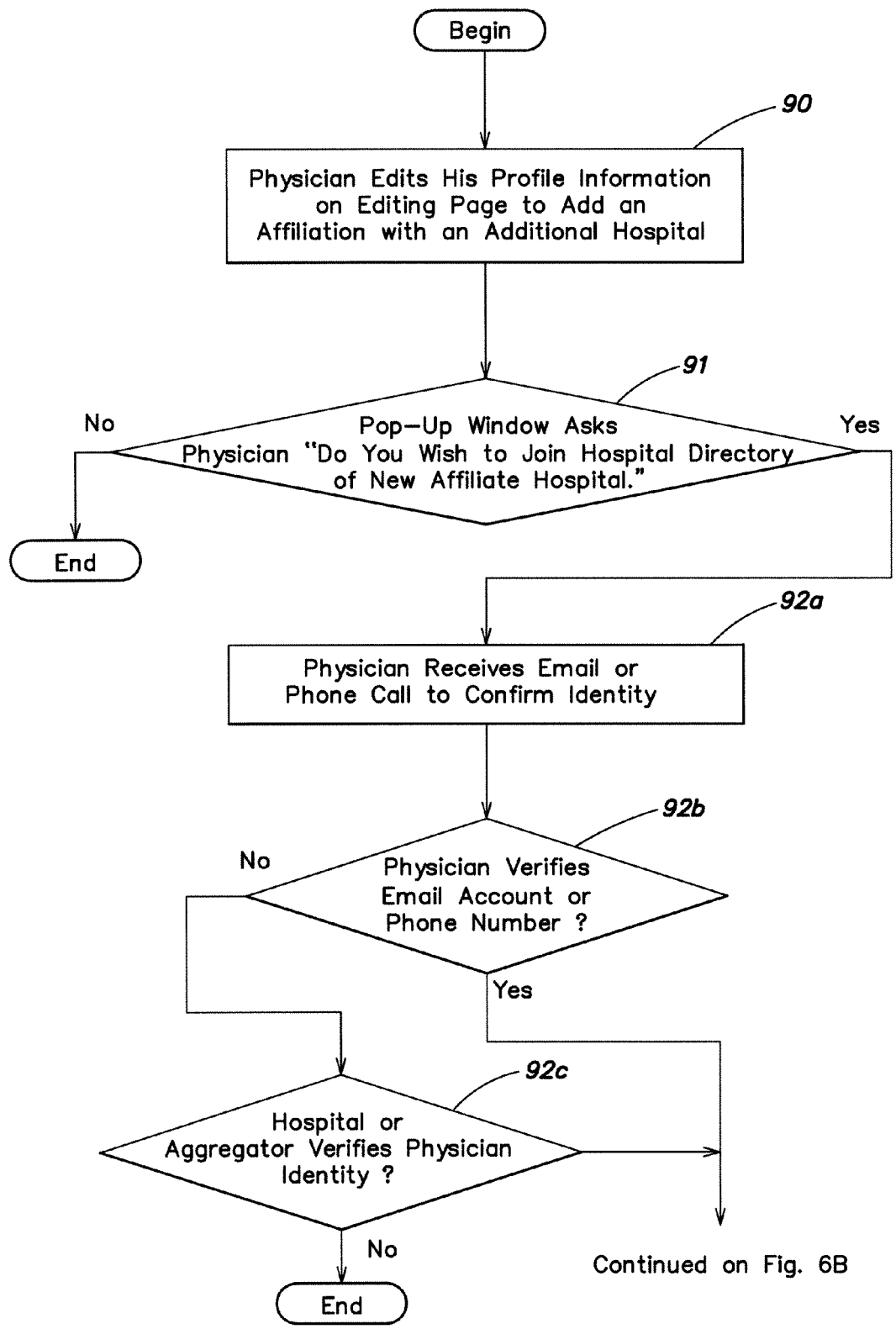
FIGS. 6a-6b is a flow diagram illustrating one example of a method for reviewing and confirming a physician's affiliation with a designated hospital prior to inclusion in the hospital directory according to one embodiment of the invention.
Figure 6B:
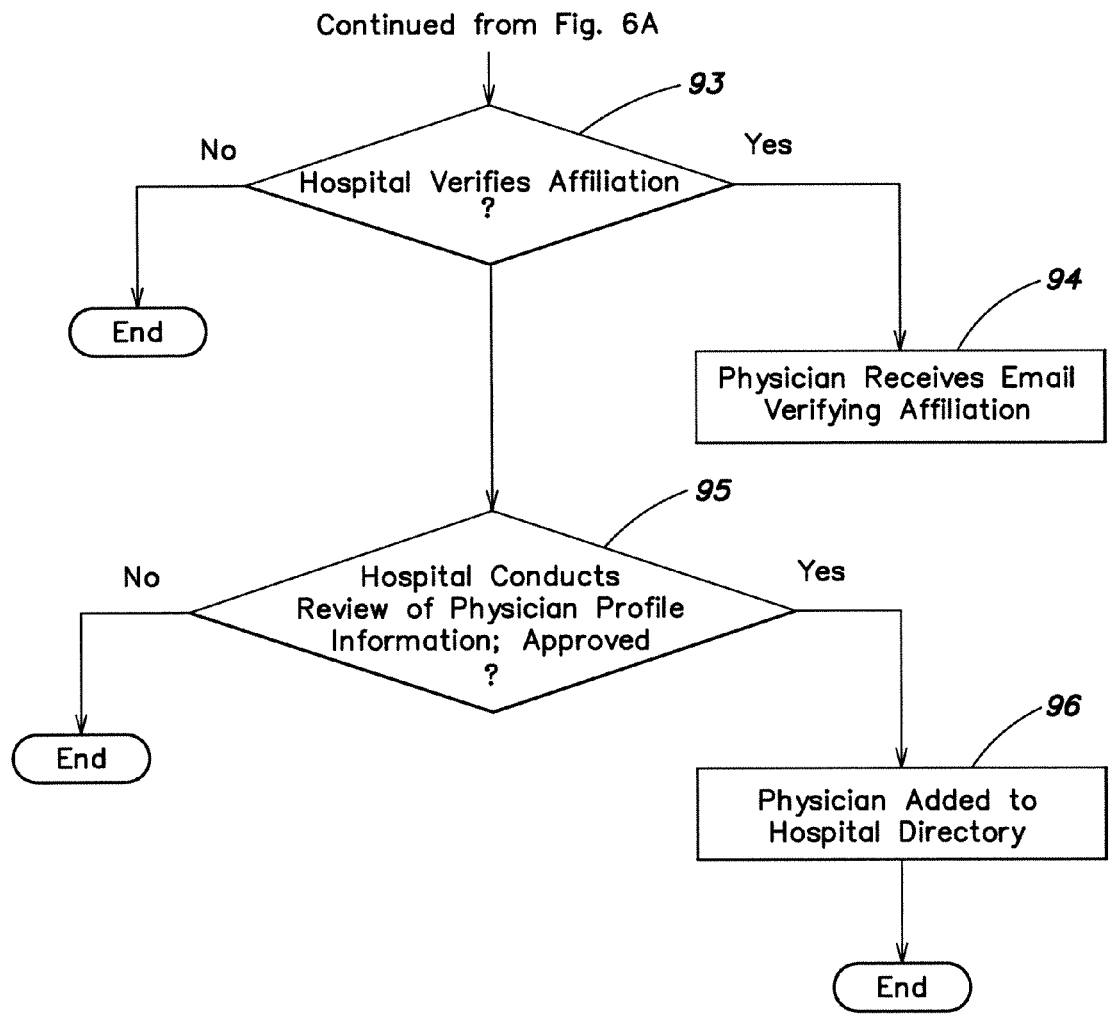

Once a physician has registered with the aggregator and is signed onto the aggregator's website, the physician can access a webpage, e.g., similar to that shown in FIG. 3, to edit his/her profile information, e.g., by clicking on the edit button 34 in the respective window of the profile information to be edited. In one example, illustrated in the flow chart of FIGS. 6a-6b, a physician has added an affiliation with an additional hospital in their profile editor on the aggregator's webpage 90. The doctor is then invited, via a popup window on the webpage, to join the hospital directory of the newly identified hospital 91. The popup window may identify the process by which this occurs, e.g.

1. The aggregator sends the physician an email or phone call to confirm his/her identify 92a; either the physician confirms the email account or phone number 92b, or the aggregator or hospital attempts to verify 92c (e.g. by calling the hospital department in which the physician practices);
2. The hospital verifies the affiliation 93;
3. The aggregator emails the physician verification of the affiliation 94;
4. The hospital credentialer reviews the submitted profile information 95; and
5. If the profile information is approved (in Step 4), the original or edited physician profile information will be added to the hospital's directory 96.

By clicking a continue button in the popup window, the physician may elect to begin this credentialing process. A new record will then appear in the hospital's credentialing process, such as that illustrated in FIG. 4. After completing an original profile entry or edit to the profile, the hospital and/or aggregator may prompt the physician to sign up for an online appointment booking process.

In another example, a physician may edit his/her profile on the aggregator's website to update or modify a particular profile data entry. In this case, the hospital credentialing reviewer will receive automatic notice (e.g., alert) of the new entry, and again will decide whether to accept or reject the entry.

Figure 7:
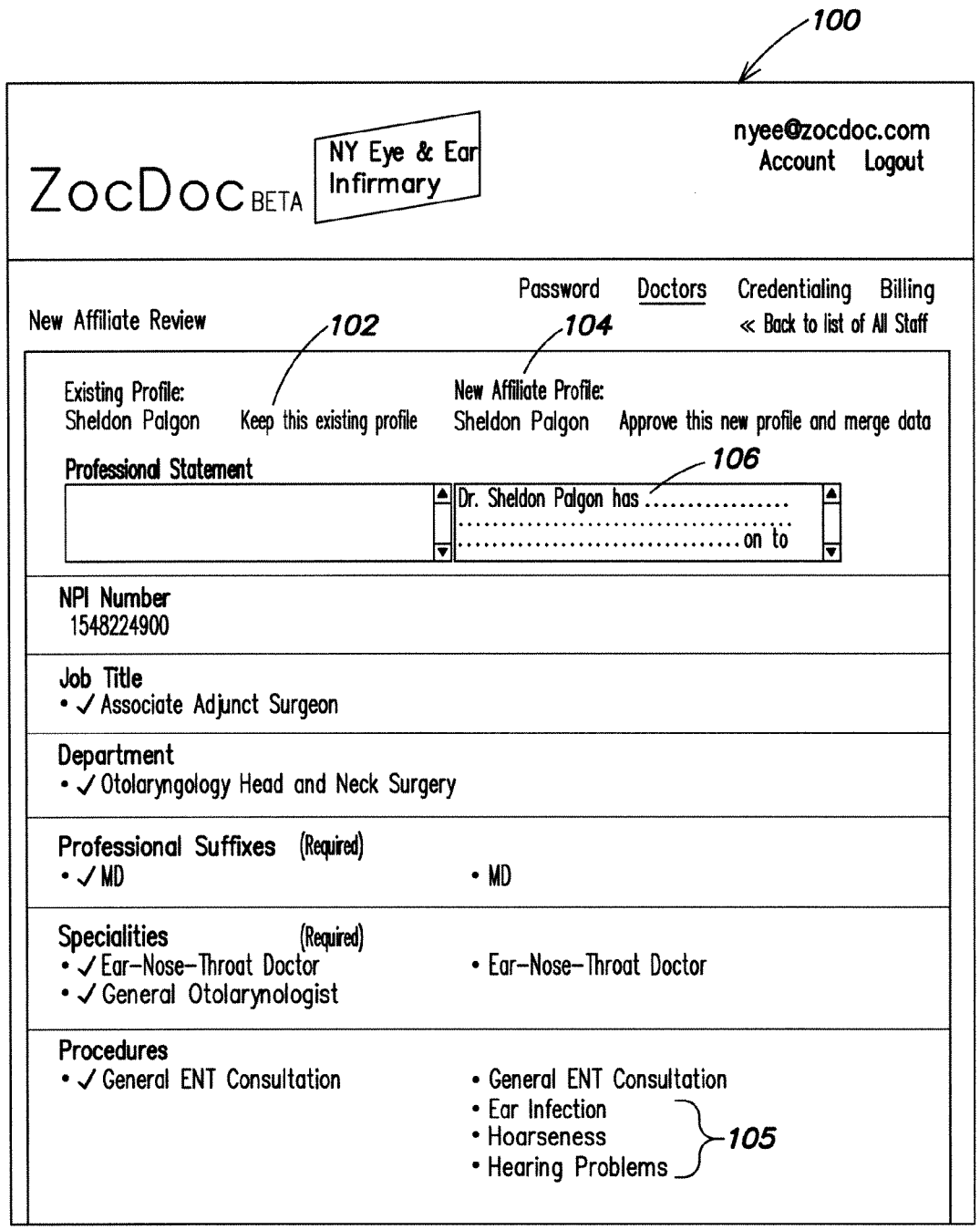
FIG. 7 is an exemplary screenshot for performing a credentialing process according to one embodiment.

FIG. 7 shows one example of a process enabling the hospital to compare new and existing profile information. In the left column of the screen 100 is the existing profile information 102 from the hospital's directory and database for the identified physician. In the right column is the new profile information 104 with each field located in the appropriate row next to the existing profile information. For example, here there are three new procedures 105 listed for this physician in the Procedures row, and a new professional statement 106 in the appropriate row. The hospital will apply its own rules for deciding whether to include, approve or reject the new procedures before merging any newly submitted procedures for inclusion on the hospital's website. All non-rejected items on the left profile (existing hospital record) have been copied to the new affiliate profile with their hospital credentialing status intact (i.e., if the hospital had previously approved an item on the existing profile, it will be approved on the new profile). All of the new affiliate data is marked as uncredentialed for the hospital. After all of the data has been copied to the new profile, the new profile is associated with the hospital and the existing profile is marked as deleted.

One important piece of profile information, especially for facilitating online booking of appointments, is the physician's insurance acceptance information. Unless this information is up-to-date and complete, a prospective patient cannot in most cases decide whether to select a particular physician i.e., a patient is unlikely to select a physician unless he knows the physician accepts his insurance plan. Thus, maintaining up-to-date insurance information in hospital directories is very beneficial if the hospital wishes to generate new patients for its affiliated physicians via its hospital directory.

In accordance with one embodiment of the invention, a process is provided for maintaining accurate and complete insurance information. Historically, there has been no common identifiers for doctors in both hospital and insurance directories, i.e., which would enable a hospital to quickly determine whether a physician affiliated with the hospital accepts a given insurance plan. For example, if a hospital has a doctor whose name is "James Smith" and there is a doctor named "James Smith" in the Aetna insurance directory, the hospital cannot be sure if this is the same James Smith and add this insurance information to the physician profile on the hospital directory. Still further, doctors do not always accept the same insurance plan at all of their locations. As a result, hospitals either do not show insurance information or they need to employ teams of people to call the doctors' offices and obtain the insurance information from the doctors' receptionists.

Not showing insurance information significantly reduces the effectiveness of a hospital directory, in terms of acquiring new patients for the hospital's affiliated physicians. Calling doctors' offices is very resource intensive and error prone, as the office staff is frequently not informed about recent changes and/or about insurance plans that have a low market share.

In accordance with one embodiment of the invention, it has been determined that a geographic location indicator can effectively enable one to determine whether or not a specific doctor matches an entry in an insurance company's online physician directory. While there may be hundreds of James Smith in New York City, it is highly unlikely there is more than one at a given location. Still further, matching doctors to insurance by name and location also solves the problem of accurately stating insurance acceptance for doctors that accept different insurance plans at different locations.

However, determining whether two locations are in fact the same is a problem in and of itself. Addresses are often spelled differently (street, st.), and often information such as suite number is omitted in some cases and is present in other cases. Thus, simple string matching of listed street addresses is not adequate to determine if two addresses are the same.

By way of example, the following three addresses may appear in different databases by a physician for a given name:

112-03 Queens Boulevard;
11203 Queens Boulevard;
11203 Queens Boulevard, Ste. 206.

If one were to try to match any of the three addresses above by string matching, it would appear that they are three distinct locations.

To solve this problem in accordance with one embodiment of the invention, a physician office location is classified by geographic coordinates, e.g. a geocode, to create a geographic location indicator which can be used to enable more accurate matching of a doctor to an insurance company's online directory entry, regardless of how common the doctor's name is. With a now reliable way to match doctors to entries in insurance directories, this process can be automated, and the aggregator and/or hospital can search insurance directories periodically for their doctors to find entries that match a specific doctor. This can be done by a computer, rather than requiring a fully staffed call center, saving many hours of work. The doctors' profiles can then be automatically updated with additional insurances, and/or the doctors can be notified that they should update their profiles to include these additional insurances. The net result is physician profiles with more accurate and up-to-date insurance information.

A geocode (Geospatial Entity Object Code) is a combination of geospatial attributes that provides an exact location of a point on the surface of the earth. Mandatory attributes included in a geocode are latitude and longitude. Other voluntary attributes are the date, local time, global time, coordinate reference system, and sensor accuracy. The aggregator can geocode the address information provided by a physician (e.g. map a street address to geographic coordinates), and also geocode the address information provided by an insurance directory, and then compare the two geocodes to determine if they match. This process can be automated by computer search, geocoding, and comparison algorithms, to produce a substantially more accurate and less error prone result than a manual comparison. Methods for geocoding are well known to a person skilled in the art and commercially available. For example, see http://code-.google.com/apis/maps/documentation/services.html#Geocoding.

Online Booking Across Multiple Websites

Doctors are reluctant to be "locked into" an online appointment booking service that is only available on one hospital website. Typically they want to provide online booking on their own group practice website. However, they also do not want to miss out on patients that might find them on an affiliated hospital directory.

There are many natural impediments to online booking of healthcare appointments across multiple websites. As with the profile information previously described, there are many variables involved in the booking of appointments which are either not understood or not consistent between different practice groups and different affiliated hospitals. Also, doctors typically have limited technical experience and expertise with implementing new software systems so any solution must be easy to implement.

In accordance with one embodiment of the present invention, apparatus and methods are provided for implementing online booking of healthcare appointments across multiple websites. An aggregator hosts an online booking functionality as a service that allows healthcare appointments to be available simultaneously on two or more of a hospital directory website, a doctor's practice group website, an insurance provider's website and an aggregator's website. Patients can book an online appointment on any of these sites and availability is updated immediately.

An online booking service is described in the previously identified co-pending and commonly owned patent applications, which are incorporated herein by reference in their entirety. As described therein, an aggregator maintains a central database and website for online booking of physician appointments across multiple practice groups. This online booking functionality can be extended to include one or more hospital websites, physician practice group websites and insurance provider websites by providing software (e.g. a Java script) embedded on the hospital and/or physician practice group and/or insurance provider websites. An example of a suitable script 110 for a physician practice group by the name "Premier Dental Associates of Lower Manhattan" is shown in FIG. 8.

JavaScript is commonly used to write functions that are embedded in or included from HTML pages and interact with the Document Object Model (DOM) of the page. The JavaScript code can run locally in a user's browser (rather than on a remote server) and thus respond to user's input actions quickly, making an application feel more responsive. In this example, the aggregator's database contains available appointment information for a plurality of practice groups, and depending upon the specific hospital or practice group website accessed by a patient, the aggregator searches for and retrieves the relevant appointment information for that practice group or affiliated doctors of the hospital. As used throughout this application, patient includes a prospective patient. In one implementation, JavaScript embedded in the practice group's website loads yet another JavaScript from the aggregator's server, which in turn fetches the appointment data from the aggregator's database and displays it on the practice group's website. This 2-layered approach makes it easier to update the underlying JavaScript and available scheduling data centrally.

Figure 9:
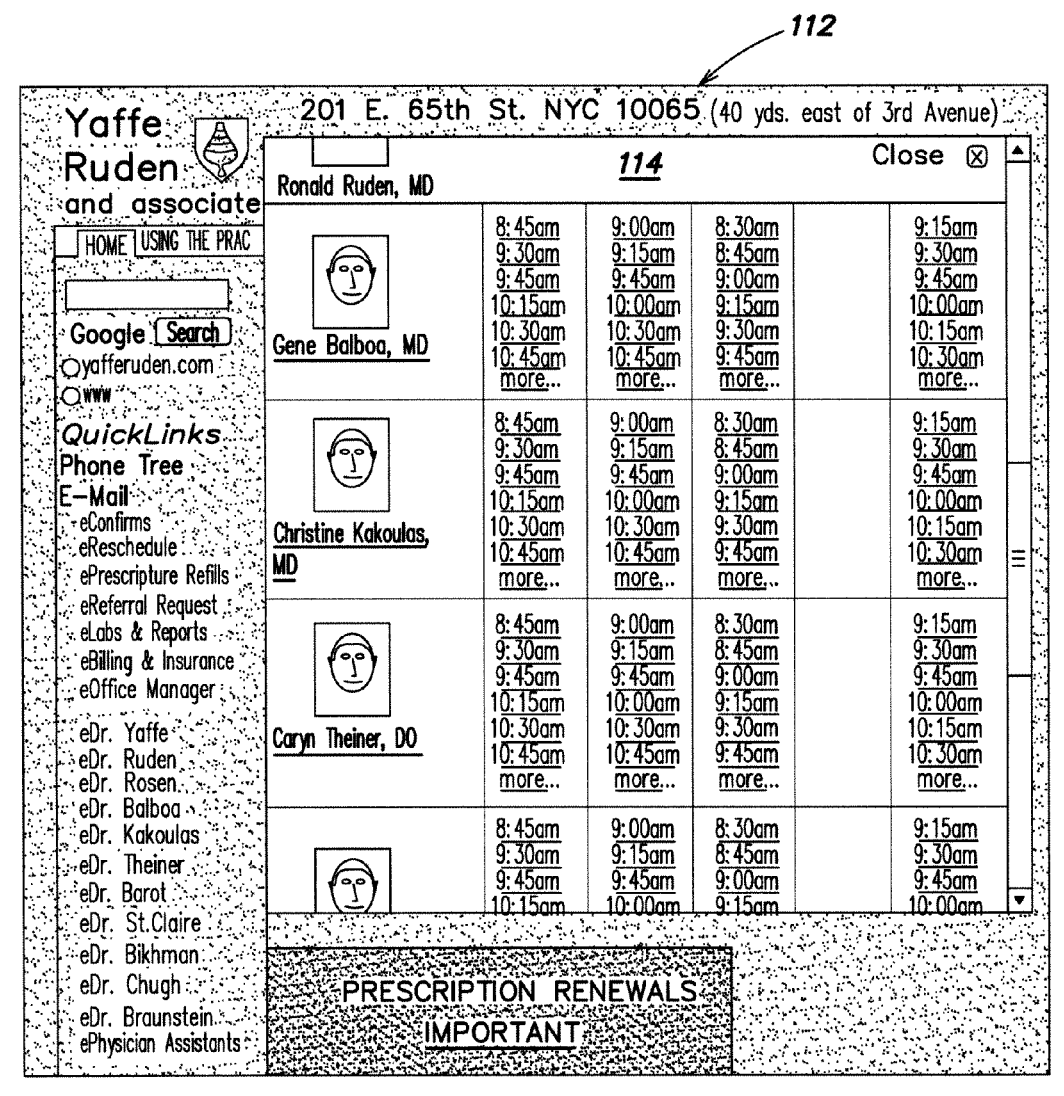

FIG. 9 illustrates one example of a doctor's website utilizing an embedded script. A home page 112 on the physician's practice group website includes a variety of descriptive information concerning the practice group. A window 114 appears on the page showing available appointment times for a plurality of physicians in the group. In this example, the physicians are listed along the left-hand margin each with a photo and a link to their profile information. To the right of each physician is an array of links with individual available appointments by date and time for that physician. Once the patient has elected a specific appointment date and time, by clicking on the link for that appointment, the patient is then connected to a webpage from the aggregator's website to complete booking of the online appointment.

As previously described, providing online booking functionality from a hospital's physician profile directory would be very desirable for hospitals (e.g., for attracting patients). However, knowing a doctor's availability is a challenge. Even if the doctor is employed by the hospital, only a minority of hospitals utilize centralized scheduling processes. For doctor's who run their own practices with their own practice management systems, this task is even more difficult. Attempts by hospital systems to incentivize doctors to migrate to the hospital scheduling system have typically failed, because it requires the physician to change their ongoing scheduling process, it locks in the doctor to a particular hospital, and the scheduling software is frequently part of a larger and more extensive practice management system (which would need to be modified).

Even access to a practice group's scheduling system is generally not sufficient to automate scheduling, as most schedules only provide "positive" information, i.e., what times the physician is booked. Much of the scheduling context, i.e., what time the doctor is in the office, which procedures can be done at which times, and which resources may be required (e.g., a special instrument) for each procedure, are generally known to the office manager and not captured in a scheduling system.

Figure 10:
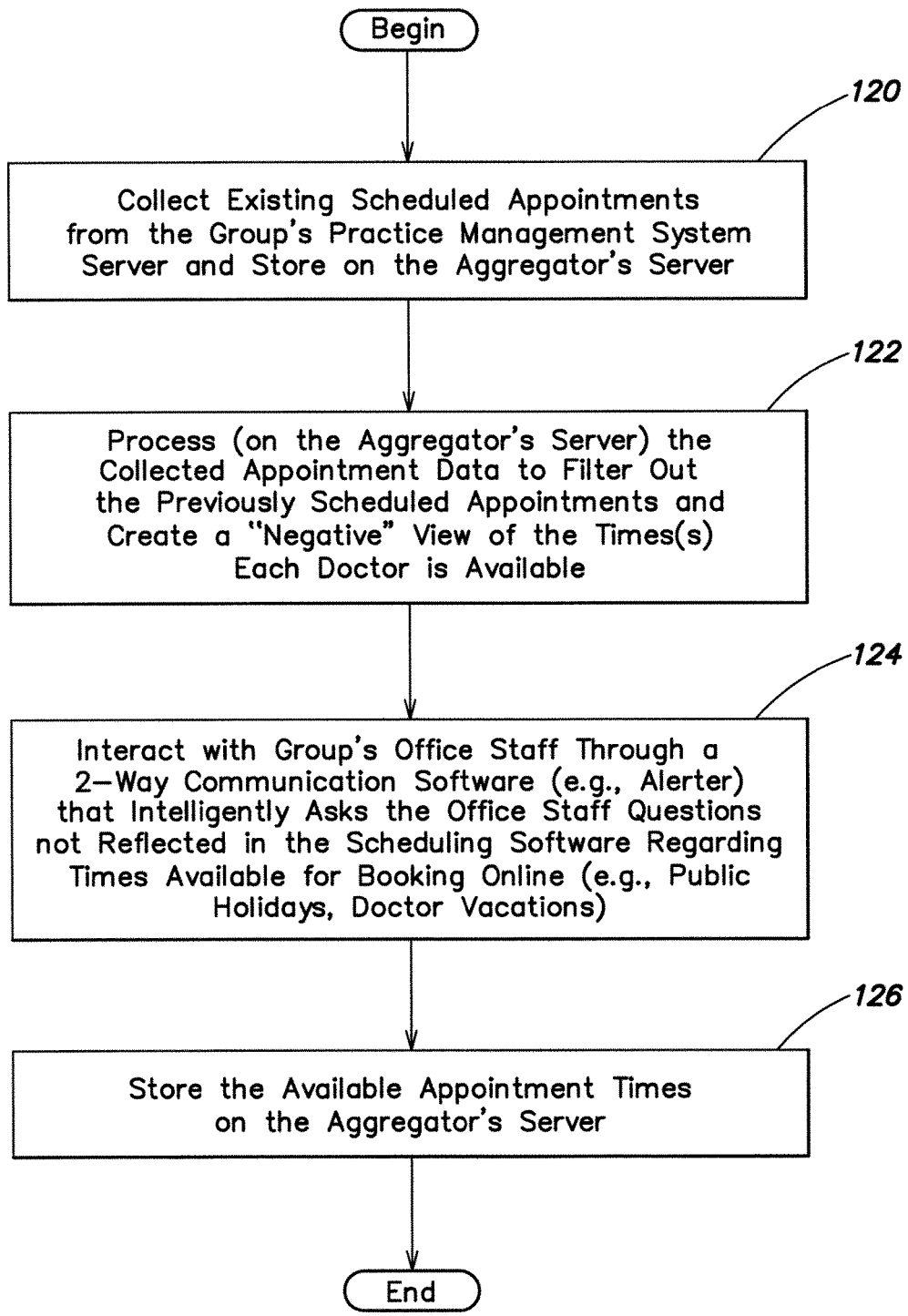
FIG. 10 is a flow diagram illustrating the operation of one embodiment of a software product for extracting appointment scheduling information from a physician's practice management system according to one embodiment of the invention.

In accordance with one embodiment of the invention, software tools are provided to enable physicians to maintain their current work flow and software processes, while information is extracted from their existing scheduling/practice management system to an aggregator's centralized server. As illustrated in the method of FIG. 10, the aggregator provides software to:

collect (read) existing scheduled appointments from a group's practice management system and store the collected data on the aggregator's server 120;
  process the collected data on the aggregator's server to filter out the previously scheduled appointment times and create a "negative" view of the time(s) the doctor(s) are available 122;
  interact with the group's office staff through a two-way communication software (e.g., "alerter") that intelligently asks the office staff questions not reflected in the scheduling software regarding times available for booking online 124, e.g., public holidays, doctor vacations; for example, the system may ask "Is the doctor working on President's Day?" a few days before the actual holiday;
  store the available appointment times on the aggregator's server 126.

Software for collecting, processing and storing such appointment data on the aggregator's server is described in the previously identified applications.

In one example, a physician practice group has its practice management system (software and data) residing in a data store in the doctor's office. A windows service (provided by the aggregator) is installed on the doctor's server that polls the doctor's practice management database to detect changes in the physician(s) schedule. In another example, the doctor's office is using a web hosted management system; in this case, the aggregator provides software that sends web requests to the hosted site, and parses the HTML that is returned to read the doctor's availability. In another example, when the physician's database server is not available, and the system is not hosted as a website, an aggregator provides software that navigates through the group's practice measurement system and captures screenshots of the doctor's schedule. The aggregator's software is able to determine availability by evaluating the color and position of the pixels in the screenshot.

The aggregator may also provide a web interface for the practice group to input variables that may not be available on the group's practice management system. These may include a physician's working hours, vacation times, appointment-specific times, location-specific times, and unavailable times in the schedule that the practice management system does not specify. The aggregator's software then creates a "negative" view of the available appointments by filtering out the times the doctor is not available.

Figure 11:
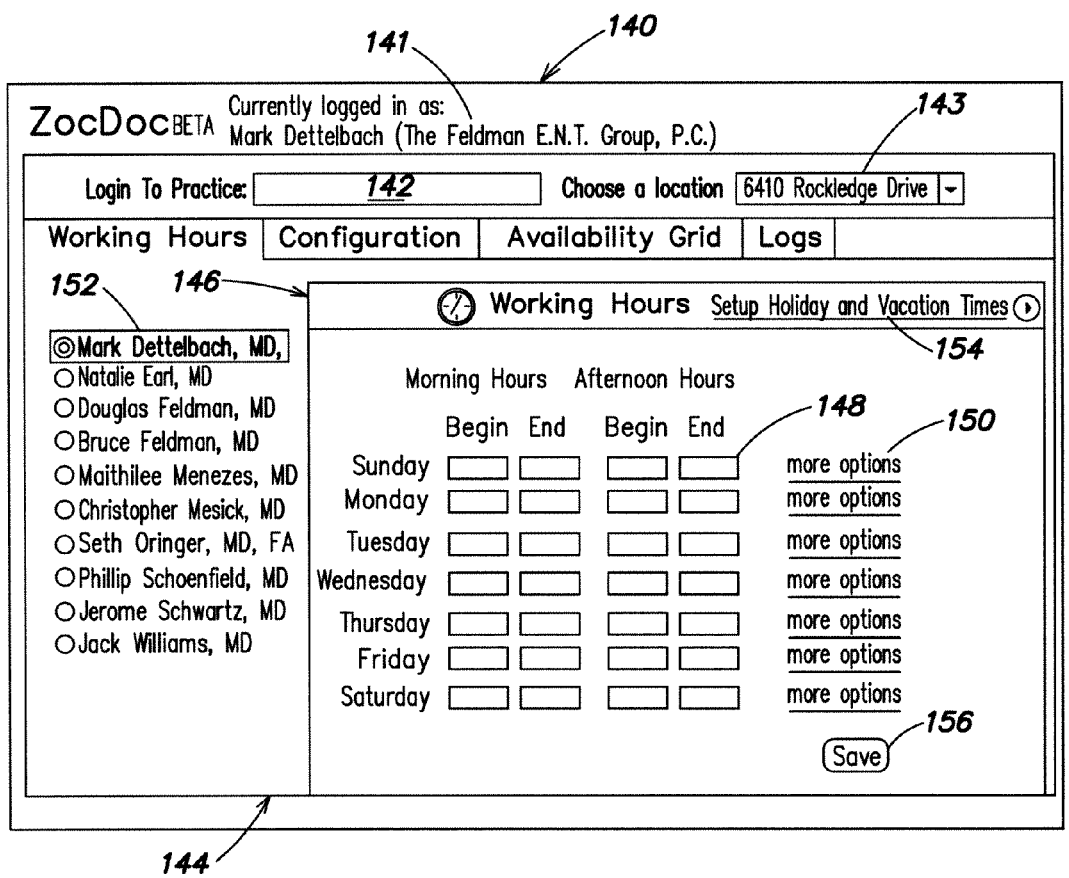
FIG. 11 is an exemplary data entry webpage enabling a physician's practice group to input appointment scheduling information to an aggregator's central database according to one embodiment.

In the following example, the practice group can input variable information to the aggregator's website, which then restricts the available appointment times that the integration software (provided on the practice group server) will upload to the aggregator's server. FIG. 11 shows a screenshot 140 on the aggregator's website for inputting such variables. At the top of the webpage, the physician and particular practice group 141 logged into the site is identified. Two windows 142, 143 enable a user to input a practice group and location. Below this, tabs 144 to alternative webpages can be selected for accessing each of Working Hours, Configuration, Availability Grid, and Logs. The Working Hour's page is displayed in a window 146 having a grid (array) of boxes 148 for inputting beginning and ending times in the morning and afternoon hours for each of the seven (7) days of the week. Links 150 are provided to select "more options" if the array provided is not sufficient. Along the left-hand margin, one particular physician in the list 152 has been designated, for which the working hours will be input. A further link 154 is provided to prompt the user to set up holiday and vacation times. Once the appropriate information has been entered, the user clicks the save button 156 to enter the information to the aggregator's database. Additional webpages may be provided for entering holiday and vacation times, location information, and procedure types.

In one embodiment, the aggregator's web interface provides an easy way to map a specific item in the local practice management system to the associated item in the aggregator's database. For example, FIG. 12 shows a screenshot 160 under the Configuration tab, for mapping location information. On the left-hand side is a list 162 of the different practice group locations as identified in the group's practice management system. These have been linked (by row) to the corresponding aggregator's location identifier in the list 164 on the right-hand side. In some cases, there is no corresponding location in the aggregator's location field, so it is marked "not mapped."

In another embodiment, if the doctor's scheduling software has the ability to make certain times available for specific procedures, the aggregator's web interface will allow the doctor to map the procedure type to the aggregator's doctor's procedure type. When a patient specifies a reason for a visit on the aggregator website, the aggregator website will then only display times that the doctor is available for that specific procedure.

Because there are many different practice management systems in use today, there are many different ways that each system implements various functions. Because the aggregator's system performs the mapping to accommodate different group software systems, each group can continue to use its respective practice management system while also providing the necessary information to synchronize the appointment availability information for booking across multiple practice groups and multiple websites.

As a further example, there is currently no standard layman's nomenclature for medical procedures, and thus searching for doctors who provide a particular procedure requires a significant amount of knowledge and investigative work on the part of the patient. Typical hospital directories are limited to listing doctors by specialty. However, not every doctor within a specialty will perform a given procedure (e.g., not all primary care doctors give flu shots), and the same procedure may be done by doctors in more than one specialty (e.g., flu shots may be given by primary care physicians, ob-gyns, pediatricians, and sometimes others). In order to give a patient an overview of his/her options, the patient would need to have an overview of all doctors who can perform a desired procedure, not limited by speciality. No accepted commercial system is currently available for patient use for this purpose.

In accordance with another embodiment of the invention, an aggregator provides a list of standardized procedures which are mapped across specialties. In the above example, if the patient searches for a flu shot after selecting ob-gyn as a specialty, primary care doctors performing this procedure will also be listed. During the profile creation, each physician indicates which procedures he/she performs.

FIGS. 13A and B shows one example of a screenshot 170 from the aggregator's database interface for implementing such mapping. The first column 172 is the specialty and sub-specialty, the second column 174 is the procedure, and the last column 176 lists all the (sub)specialties that can potentially offer the procedure listed in the second column. Thus, for any given specialty/procedure pair in the first two columns (i.e., for each row of the database shown in FIGS. 13A and B), when one or the other is selected by the patient the last column indicates all of the specialties and sub-specialties that should be searched to determine which physicians can perform the desired procedure, despite the patient failing to request the specialty. This organization of the database and search process on the aggregator's database enables an identification of doctors who provide the desired service, irrespective of their specialty or sub-specialty.

Insurance Providers

The previously described embodiments were directed to hospital directories containing profiles of physicians with multiple hospital affiliations. These embodiments are equally applicable to insurance provider directories containing profiles of physicians with multiple insurance participations. Such alternative embodiments will not be repeated herein, but rather the prior embodiments should be understood to include an insurance directory instead of a hospital directory, or both an insurance directory and hospital directory. Thus, the aggregator's central database, online booking functionality and credentialing software, can be run concurrently for one or more of multiple hospitals, multiple insurance providers, or both.

As previously described, insurance companies have a great incentive to facilitate patient access to a physician within the insurer's network of approved physicians, e.g., to comply with statutes that may require the insurer to provide an appointment within a specified time and/or to reduce the high cost of emergency room visits by instead providing an appointment with a physician in the physician's office. The categories of physician profile information provided on an insurance directory may typically include, in addition to those previously identified, the doctor's gender, the hospital affiliation(s), name, and office location(s). The previously described credentialing process is also of great benefit to insurers as strict credentialing requirements are often imposed by state law on insurance providers.

Thus, it should be understood that all of the previous embodiments are equally applicable to insurance provider directories and booking of appointments on the insurers' websites.

System, Method and Computer Program

As will be appreciated by one skilled in the art, the present invention may be embodied as an apparatus or method, including a computer system or computer program product. Accordingly, unless specified to the contrary, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code stored in the medium.

Any combination of one or more computer-usable or computer-readable medium(s) may be utilized, unless specified to the contrary herein. The computer-usable or computer-readable medium may be, for example but not limited to, electronic, magnetic, optical, electromagnetic, infrared, or semiconductor storage mediums. More specific examples (a non-exhaustive list) include: a portable computer diskette, a hard disk, a random access memory (RAM), a read-only memory (ROM), an erasable programmable read-only memory (EPROM or Flash memory), a portable compact disc read-only memory (CDROM), an optical storage device.

Computer program code for carrying out operations of the present invention may be written in any combination of one or more programming languages, including an object oriented programming language such as Java, Smalltalk, C++, C#, JavaScript/Ajax and similar programming languages. JavaScript, which relies on a runtime environment in a web browser, is commonly used for website development (e.g., writing functions that are embedded in or included from HTML pages). JavaScript can be used as a scripting language for implementing an Ajax-embedded webpage. Unless otherwise specified, the program code may execute entirely on a user's computer, partly on the user's (e.g., server or client) computer, as a stand-alone software package, partly on a user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A website is a collection of web pages posted on one or more web servers, accessible via the Internet. A webpage is a document, typically written in [X]HTML, that is generally accessible via HTTP, a protocol that transfers information from a web server to a display in the user's web browser. The collection of publically accessible websites are referred to as the "World Wide Web".

Websites are written in, or dynamically converted to, HTML (hyper text mark-up language) and are accessed using a software interface known as the user agent. Web pages can be viewed or otherwise accessed from a range of computer-based and Internet-enabled devices of various types, including desktop computers, laptop computers, PDA's and cell phones. A website is posted on a computer system known as a web server, and it includes software that retrieves and delivers the pages in response to requests from the website users.

A dynamic website presents variable information that is tailored to particular users. It may accept the user's input and respond to a user's request. For example, the user can enter text into a data entry field or form or select highlighted (linked) options, which prompts the website to fulfill the request and return a unique result. The aggregator's website, accessible in various forms to patients, hospitals, insurers and practice groups, includes such dynamic functionality.

A link or hyperlink, is a reference or navigation component in a document to another section of the same document or to another document on a different domain. A web browser usually displays a link in some distinguishing way, e.g. in a different color, font or style. When the user activates the link (e.g. by clicking on it with the mouse) the browser will display the target of the link.

As used herein, database and central database are not meant to be limiting, and may reside in one or more locations and/or data repositories. The aggregator's database is referred to as a central database to distinguish it from the separate multiple databases of the unaffiliated practice groups from which the aggregator combines (aggregates) the available appointment times to be offered on the aggregator's website.

The aggregator can, by collecting and storing this available appointment data from a plurality of unaffiliated practice groups, provide a much larger database of available appointment times/specialties/procedures and can allow patients to book appointments directly with the aggregator, without requiring the patients to contact the practice group in any manner (by phone, email or practice group website).

The present invention is described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The flowchart and block diagrams illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

By way of example only, various described embodiments may be implemented on processor based servers, such as any x86_64 processor based server, for example running a Windows Operating System, e.g. Windows Server 2003, Windows XP/Vista, including Microsoft's NET Framework (e.g. Net 2.0). The database programming may be implemented in the SQL programming language (e.g. MS SQL 2005 and TSQL).

Modifications can be made to the previously described embodiments of the present invention and without departing from the scope of the invention, the embodiments being illustrative and not restrictive.

The invention claimed is:

1. A method of managing a physician profile data aggregator server comprising:
    maintaining a central managed database of profile information for physicians having affiliations with multiple hospitals and insurance providers, wherein the multiple hospitals and insurance providers have multiple respective online directories of profile information and have different sets of credentialing rules, each set of credentialing rules for a given hospital or insurance provider specifying a subset of the profile information that is compliant for inclusion in the respective online directories of physicians affiliated with the given hospital or insurance provider;
    the aggregator's server providing a web page to a client computer, the web page serving as a template for entry of physician profile data and having a plurality of data fields for entering items of profile information according to a data entry mask, said data fields being standardized so that data can be used across multiple hospitals/insurance providers;
    receiving input adding an affiliation of the physician with an additional hospital and/or insurance provider;
    searching for an additional set of credentialing rules required for the additional hospital and/or insurance provider and adding dynamically updating the data fields of the data entry mask to generate an updated data entry mask for the additional hospital and/or insurance provider comprising an intersection of the set of the plurality of data fields and the subset of profile information determined by the additional set of credentialing rules to be compliant for inclusion in a respective online directory of the additional hospital/insurance provider;
    receiving physician profile data at the web page and storing a record of physician profile information in the central database;
    providing the physician profile information from the central database for inclusion in various online physician profile directories of the hospitals/insurance providers with which the physician is affiliated; and
    applying the set of credentialing rules specific to the hospital or insurance provider in order to determine compliance with the rules of some or all of the profile information, wherein said rules comprise criteria for determining whether individual ones of said data fields are automatically excluded from an online directory of the respective hospital or insurance provider, automatically included in the online directory, and require approval prior to being included in the online directory;
    including the profile information for which compliance is found in the online directory of the respective hospital or insurance provider; and
    mapping physician availability between an availability aggregator system and a practice management system to provide a view of physician availability, where mapping comprises installing a program on the practice management system that captures a screenshot showing at least one of physician availability and unavailability times and transmits the screenshot to the availability aggregator system that determines at least one of physician availability and unavailability times by evaluating color and position of one or more pixels in the screenshot.

2. The method of claim 1, further comprising:
    comparing the provided profile information to the hospital's or insurance provider's existing physician profile information and applying a merge process to create a merged profile.

3. The method of claim 1, further comprising: allowing shared access to the profile information as a web-based service.

4. The method of claim 1, further comprising: the aggregator managing a central database of available appointments with the physicians and providing online booking of available appointments with the physicians.

5. The method of claim 4, further comprising:
simultaneously providing the available appointments for online booking on a plurality of websites hosted by two or more of the aggregator, hospital, insurance provider, and/or physician practice group.

6. The method of claim 4, further comprising: providing a link in the hospital or insurance provider directory to the online booking process.

7. The method of claim 1, wherein the aggregator manages and provides multiple such directories, each for a different hospital.

8. The method of claim 7, wherein the aggregator manages credentialing of the physician profile information prior to inclusion of the profile information in the directory.

9. The method of claim 7, wherein each directory provides online booking of appointments with the hospital's respective affiliated physicians.

10. The method of claim 1, wherein the aggregator manages a central database of available appointments for physicians affiliated with multiple hospitals.

11. The method of claim 1, further comprising: providing a hospital directory of the physician profile information for physicians affiliated with the hospital.

12. The method of claim 1, wherein the physicians:
have affiliations with multiple hospitals;
practice in multiple practice groups; and/or
participate with multiple insurance providers;
and the profile information undergoes a credentialing process specific to each
affiliated hospital, practice group or insurance provider prior to inclusion in a directory of the respective hospital, group or provider.

13. The method of claim 1, wherein the physicians:
have affiliations with multiple hospitals;
practice in multiple practice groups; and/or
participate with multiple insurance providers;
and the online booking process is available on multiple websites of the hospital(s), group(s) and provider(s).

14. A physician profile management apparatus comprising:
a computer apparatus including a processor and memory storing one or more programs for execution by the processor;
a storage module for storing in an aggregator's central managed database physician profiles for physicians having affiliations with multiple hospitals and/or insurance providers, wherein the multiple hospitals and insurance providers have multiple respective online directories of profile information and have different sets of credentialing rules, each set of credentialing rules for a given hospital or insurance provider specifying a subset of the profile information that is compliant for inclusion in the respective online directories of physicians affiliated with the given hospital or insurance provider;
a template module executed by the processor for delivering a web page to a client computer over a public network, the web page serving as a template for physicians to submit the profile information to the database; and
a selection filter executed by the processor for retrieving from the database different select categories of the profile information for a specified physician, based on the affiliated hospital/insurance providers for each physician, whereby the web page has a plurality of data fields according to a data entry mask, said data fields being standardized so that data can be used across multiple hospitals/insurance providers;
the apparatus configured so that when input is received from a physician adding an affiliation with an additional hospital and/or insurance provider, an additional set of credentialing rules for the additional hospital and/or insurance provider is retrieved and the data fields of the data entry mask are dynamically updated to generate an updated data entry mask for the additional hospital and/or insurance provider, the updated data entry mask comprising an intersection of the set of the plurality of data fields and the subset of profile information determined by the additional set of credentialing rules as compliant for inclusion in a respective online directory of the additional hospital/insurance provider, the apparatus being configured to receive physician profile data at the web page, store a record of physician profile information in the aggregator's database and provide the physician profile information from the central database for inclusion in various online physician profile directories of the hospitals/insurance providers with which the physician is affiliated, and a credentialing module executed by the processor for applying credentialing rules specific to a hospital or insurance provider for application to the profile information prior to inclusion of the profile information in an on-line physician profile directory of the respective hospital or insurance provider, wherein said rules comprise criteria for determining whether individual ones of said data fields are automatically excluded from an online directory of the respective hospital or insurance provider, automatically included in the online directory, and require approval prior to being included in the online directory; and
a physician availability mapping module for mapping between an availability aggregator system and a practice management system to provide a view of physician availability, where the mapping module comprises a program module installed on the practice management system that captures a screenshot showing at least one of physician availability and unavailability times and transmits the screenshot to the availability aggregator system that determines at least one of physician availability and unavailability times by evaluating color and position of one or more pixels in the screenshot.

15. The apparatus of claim 14, wherein the fields comprise one or more of:
physician name;
phone number;
practice location;
office hours;
title;
department;
professional suffixes;
board membership;
gender;
specialties;
procedures performed;
insurances;
awards;
publications;
practice location; and
a geographic indicator of the practice location.

16. The apparatus of claim 14, further comprising: a central managed database of available appointments with the physicians.

17. The apparatus of claim 16, further comprising: a web portal accessible by computer to patients over a public network for booking one of the available appointments.

18. The apparatus of claim 17, wherein the hospital or insurance provider directory includes a link to the web portal providing online booking of appointments with physicians.

* * * * *